(12) United States Patent
Guo (10) Patent No.: US 12,324,673 B2
(45) Date of Patent: Jun. 10, 2025

(54) MULTIFUNCTIONAL ELECTRIC WAVE GENERATOR FOR SIMULATION OF BRAIN WAVE AND CONTROL METHOD THEREOF

(71) Applicant: Hangyu Guo, Guangdong (CN)

(72) Inventor: Hangyu Guo, Guangdong (CN)

( * ) Notice: Subject to any disclaimer, the term of this patent is extended or adjusted under 35 U.S.C. 154(b) by 0 days.

(21) Appl. No.: 18/765,181

(22) Filed: Jul. 5, 2024

(65) Prior Publication Data
US 2024/0358313 A1    Oct. 31, 2024

(30) Foreign Application Priority Data

Jun. 18, 2024 (CN) .......................... 202410790184.X (51) Int. Cl.
| | |
|---|---|
| *A61B 5/369* | (2021.01) |
| *A61M 21/02* | (2006.01) |
| *A61N 1/36* | (2006.01) |
| *A61N 2/02* | (2006.01) |
| *G16H 50/50* | (2018.01) |

(52) U.S. Cl.
CPC ............. *A61B 5/369* (2021.01); *A61M 21/02* (2013.01); *A61N 1/36025* (2013.01); *A61N 2/02* (2013.01); *G16H 50/50* (2018.01)

(58) Field of Classification Search
None
See application file for complete search history.

(56) References Cited

U.S. PATENT DOCUMENTS 4,806,881 A * 2/1989 Ives .................... G06F 7/544
                                                327/107

FOREIGN PATENT DOCUMENTS

CN        209374057 U  *  9/2019

OTHER PUBLICATIONS

Sanus. (2014). CFR2115, CFR2127, CFR2136, CFR2144 Instruction Manual. Sanus CFR2144. https://www.sanus.com/assets/products/cfr2144/documents/CFR21XX_6901_002396_rev01.pdf (Year: 2014).*
Leger, G. (Oct. 9, 2017). How to use a function generator. Simply Smarter Circuitry Blog. https://www.circuitspecialists.com/blog/how-to-use-a-function-generator/ (Year: 2017).*

(Continued)

*Primary Examiner* — Charles A Marmor, II
*Assistant Examiner* — Marc D. Honrath
(74) *Attorney, Agent, or Firm* — JEEN IP LAW, LLC (57) ABSTRACT

Provided herein are a multifunctional electric wave generator for simulation of brain wave and a control method. The multifunctional electric wave generator for simulation of brain wave includes a base, a protective box fixedly mounted on the top of the base, a support plate located inside the protective box, an electric wave generator body placed on the support plate, consisting of a housing, a signal receiver, a frequency controller, a power amplifier, a waveform converter, an output device, and a digital signal processor; the signal receiver, frequency controller, power amplifier, waveform converter, output device, and digital signal processor are all assembled inside the housing and are interconnected electrically, and a storage mechanism disposed on the protective box for storing the electric wave generator body.

8 Claims, 10 Drawing Sheets

(56) References Cited

OTHER PUBLICATIONS

Al-Samman, A. M., Abd. Rahman, T., & Al-Hadhrami, T. (2019). Comparative study of indoor propagation model below and above 6 ghz for 5G Wireless Networks. Electronics, 8(1), 44. https://doi.org/10.3390/electronics8010044 (Year: 2019).*

Accuride 2019 75-lb. Drawer Slides, Rockler.com. (Aug. 16, 2022). http://rockler.com/accuride-2019-75-lb-drawer-slides-with-brackets-for-suspended-mounting (Year: 2022).*

* cited by examiner

MULTIFUNCTIONAL ELECTRIC WAVE GENERATOR FOR SIMULATION OF BRAIN WAVE AND CONTROL METHOD THEREOF

CROSS-REFERENCE TO RELATED APPLICATIONS

This application claims priority to Chinese patent application No. 202410790184X, filed on Jun. 18, 2024, which is hereby incorporated by reference in its entirety.

TECHNICAL FIELD

The present disclosure relates to the field of electric wave generators, and in particular to a multifunctional electric wave generator for simulation of brain wave and control method thereof.

BACKGROUND

Electric wave generator for simulation of brain wave is a device capable of simulating human brain wave signals and generating fluctuating magnetic or electric fields of corresponding frequency and amplitude. It generates an electric field through coupling coils or flat electrodes to simulate human brain wave signals, producing fluctuating magnetic fields or electric fields of a certain frequency and amplitude, exerting a close-range act on the human brain. It gradually reduces the degree of excitement in a certain pattern, inducing sleep.

At present, most of the existing electric wave generators can only induce people to enter sleep by simulating brain wave signals, but they are unable to stimulate brain activity to enhance focus for work or study efficiently, which limits their versatility.

SUMMARY

The present disclosure provides a multifunctional electric wave generator for simulation of brain wave and control method thereof, aiming to solve the problem that the existing electric wave generators are unable to adjust simulated brainwave signals according to the user's needs as mentioned in the background art.

The technical solution of the present disclosure is implemented as follows:

The present disclosure provides a multifunctional electric wave generator for simulation of brain wave, including a base, a protective box fixedly mounted on the top of the base, a support plate located inside the protective box, an electric wave generator body placed on the support plate, and a storage mechanism disposed on the protective box for storing the electric wave generator body.

The electric wave generator body includes a housing, a signal receiver, a frequency controller, a power amplifier, a waveform converter, an output device, and a digital signal processor. The signal receiver, frequency controller, power amplifier, waveform converter, output device, and the digital signal processor are all assembled inside the housing and are interconnected electrically.

Optionally, a limit plate is fixedly mounted on one side of the electric wave generator body, an L-shaped plate is fixedly mounted on the top of the support plate, the L-shaped plate is slidingly connected to the limit plate, and a screwing rod is threadedly mounted on the top of the limit plate, and the screwing rod is threadedly connected to the L-shaped plate.

Optionally, the storage mechanism includes a connecting box fixedly mounted on the upright posts of the base, a threaded rod rotatably mounted at the top of the connecting box, a threaded sleeve set on the threaded rod, a connecting plate fixedly mounted on one side of the support plate, and a drive mechanism provided on the connecting box for driving the threaded rod.

One side of the connecting plate extends outside of the protective box, and the connecting plate is securely connected to the threaded sleeve.

Optionally, the drive mechanism includes a connecting piece fixedly mounted in the connecting box, a rotating lever rotationally mounted on the connecting piece, a junction box fixedly mounted on one side of the connecting box, a first sprocket fixedly socketed to the rotating lever, connected to a first chain that passes through the junction box and meshes with the first sprocket, a first motor fixedly mounted at the bottom of the connecting box, a set of drive gears fixedly socketed to the output shaft of the first motor and the rotating lever respectively, withe the drive gears meshing with each other.

The the rotating lever and the threaded rod are both fixedly sheathed with conical gears, with a set of the conical gears meshing with each other.

Optionally, the top of protective box is in an opening shape, a cover plate is hingedly connected to the top of the protective box, the top of the cover plate is fixedly mounted with a handle, and the top of the electric wave generator body is assembled with a push rod.

Optionally, a notch is provided on one side of the protective box, the notch is adapted to the connecting plate.

Optionally, one side of the connecting box is fixedly equipped with a mounting tab, on which a connecting bar is pivotally mounted, the connecting bar is wrapped with a rope, the top end of the rope is fixedly connected to one side of the cover plate.

Optionally, the connecting bar and rotating lever are both equipped with a second sprocket, and a second chain is wrapped around the two second sprockets, engaging with both of them.

Optionally, a protective cover is fixedly mounted on the mounting tab, and the protective cover is placed on the second sprocket located on the connecting bar.

On the other hand, the present disclosure further provides a control method of a multifunctional electric wave generator for simulation of brain wave, comprising the following steps:

Step one: Ensuring the power supply is stable, connecting the power and ground lines correctly, activating the electric wave generator and allowing it to warm up to improve the frequency stability.

Step two: Selecting or setting a modulation mode as needed, which includes amplitude modulation, frequency modulation, and phase modulation, choosing appropriate filters to filter out clutter or noise from the output signal, then setting or adjusting various parameters, such as waveform type, frequency, amplitude, through a microprocessor to ensure stable DC power supply to the internal circuit of the electric wave generator body.

Step three: Selecting the desired waveform type through a waveform converter, which includes sine wave, square wave, and triangle wave, setting the desired range of signal output frequency range by a frequency controller, adjusting a fine-tuning knob or a keyboard to input the precise frequency, adjusting the output power of the power amplifier as needed to ensure sufficient signal strength, and monitoring the waveform, frequency, amplitude, and other parameters of the output signal in real-time through a display device, utilizing a digital signal processor to further process and optimize the output signal.

Compared with the prior art, the multifunctional electric wave generator for simulation of brain wave and control method thereof in the present disclosure have the following beneficial effects:

Trough combining the electric wave generator with an artificial intelligence (AI) monitoring system, and then setting the intensity of the wave type and the duration required by the user, it is possible to effectively release different levels of brainwave signals to the user. The electric wave generator body is stabilized in the support plate through the sliding connection between the limit plate and the L-shaped plate, which effectively prevents the displacement during operation due to vibration or external forces; and the wave generator body can be stored by the storage mechanism for protection, ensuring its safety when not in use and providing effective protection.

Through the dual transmission of conical gears and the first chain, the drive mechanism efficiently transfers the power from the first motor to the threaded rod, ensuring the quick storing and unfolding of the wave generator body. By pushing out the cover plate with the top rod, the cover plate is rotated away from the protective box, allowing for automatic closing of the cover plate, making the operation more convenient. By combining the notch with the connecting plate, the connecting plate can be retracted effectively, reducing the entry of external dust into the protective box.

By winding the rope around the connecting bar, the cover plate can be automatically opened and closed without manual intervention, offering a better user experience. Driving the second sprocket to rotate through the second chain, which then synchronously drives the rotating lever to pivot the connecting bar, enables the synchronous release or retraction of the rope and threaded barrel, effectively reducing operating costs. By using a protective cover to protect the second sprocket and the second chain, ensuring that external dust does not come into contact with them, thus helping to mitigate wear and tear. The wire pulley is used to guide the rope, ensuring smooth sliding and facilitating the opening and closing of the cover plate.

Compared with the existing technologies, the multifunctional electric wave generator for simulation of brain wave and control method thereof in the present disclosure can simulate various waveforms, making it suitable for different user groups, and demonstrating high applicability.

DETAILED DESCRIPTION OF THE EMBODIMENTS

Unless otherwise defined, all technical and scientific terms used in this disclosure have the same meaning as understood by those skilled in the art in the field to which this application pertains. The terms used in the specification of this disclosure are intended for the purpose of describing specific embodiments and not to limit the scope of this disclosure. The terms "comprising" and "having," and any variations thereof in the specification and claims of this disclosure or the accompanying drawings, are intended to encompass non-exclusive inclusions. The terms "first," "second," etc., used in this disclosure's specification and claims, or in the accompanying drawings, are used to distinguish different objects and not to describe specific sequences. The directional or positional relationships indicated by terms such as "inner," "outer," "left," "right" are based on the orientation or positional relationships shown in the drawings, solely for the purpose of describing and simplifying the description of the disclosure, and do not imply that the devices or components referred to must have specific orientations, be constructed or operated in a specific orientation, and therefore should not be construed as limiting the scope of the disclosure.

Reference to "embodiments" in this disclosure means that the specific features, structures, or characteristics described in conjunction with the embodiments may be included in at least one embodiment of this disclosure. The appearance of this phrase at various points in the specification does not necessarily refer to the same embodiment each time and is not mutually exclusive or alternative embodiments that are independent of or contradictory to other embodiments. It is understood explicitly and implicitly by those skilled in the art that the embodiments described in this disclosure can be combined with other embodiments.

Referring to FIGS. 1-12 shown, a multifunctional electric wave generator for simulation of brain wave of present embodiment includes a base 1, a protective box 2 fixedly mounted on the top of the base 1, a support plate 3 located inside the protective box 2, an electric wave generator body 4 placed on the support plate 3, and a storage mechanism disposed on the protective box 4 for storing the electric wave generator body 4.

Figure 1:
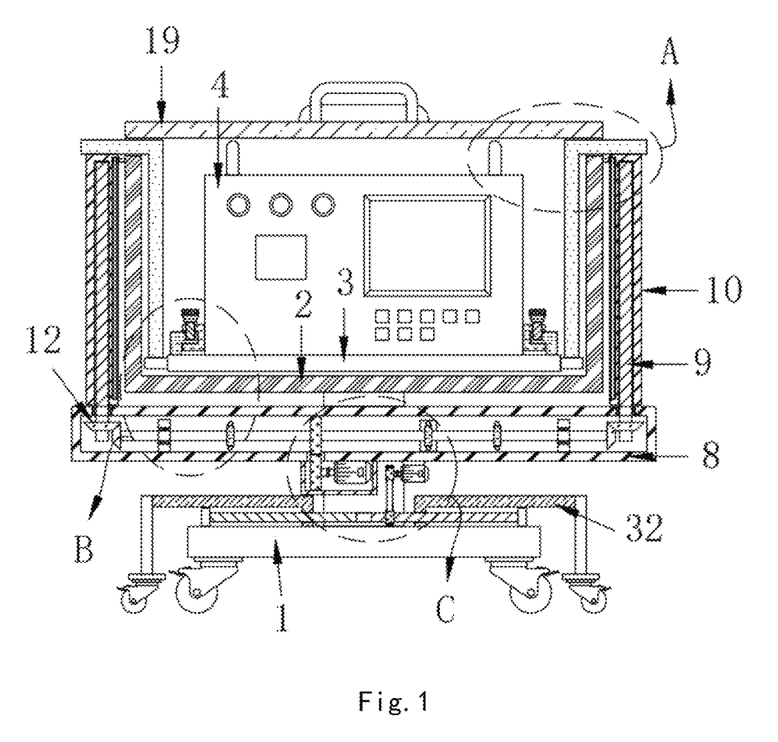
FIG. 1 is a schematic front cross-sectional structural view of a multifunctional electric wave generator for simulation of brain wave and control method thereof in the present disclosure.
Figure 2:
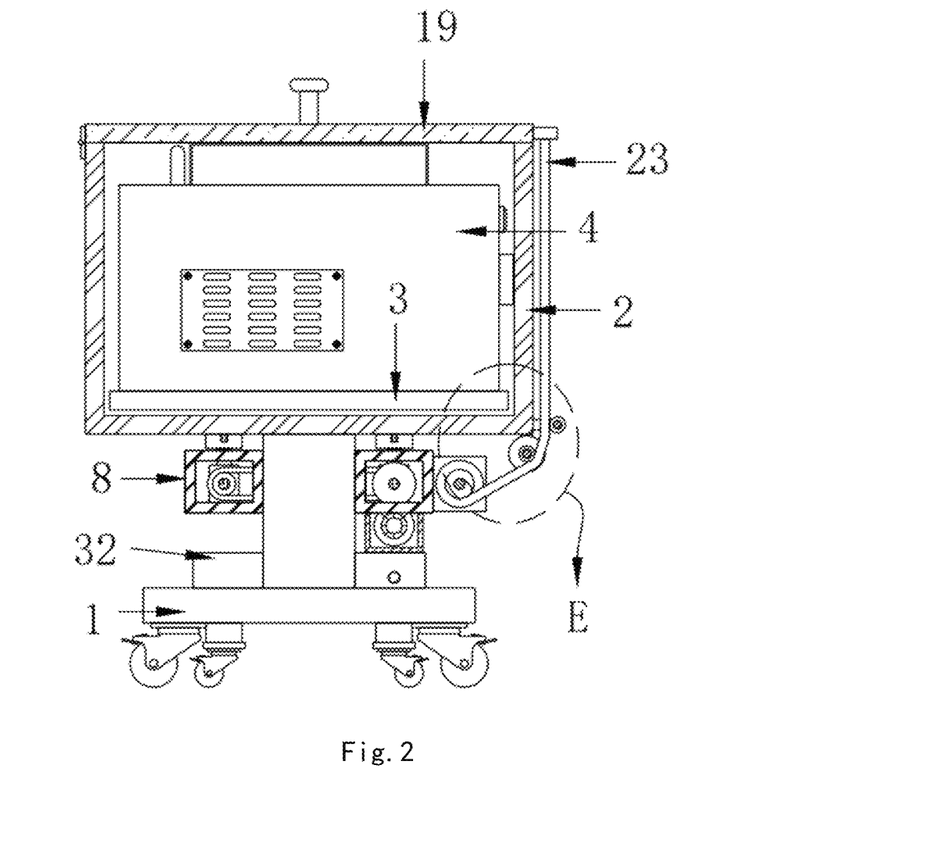
FIG. 2 is a schematic side cross-sectional structural view of a multifunctional electric wave generator for simulation of brain wave and control method thereof in the present disclosure.
Figure 3:
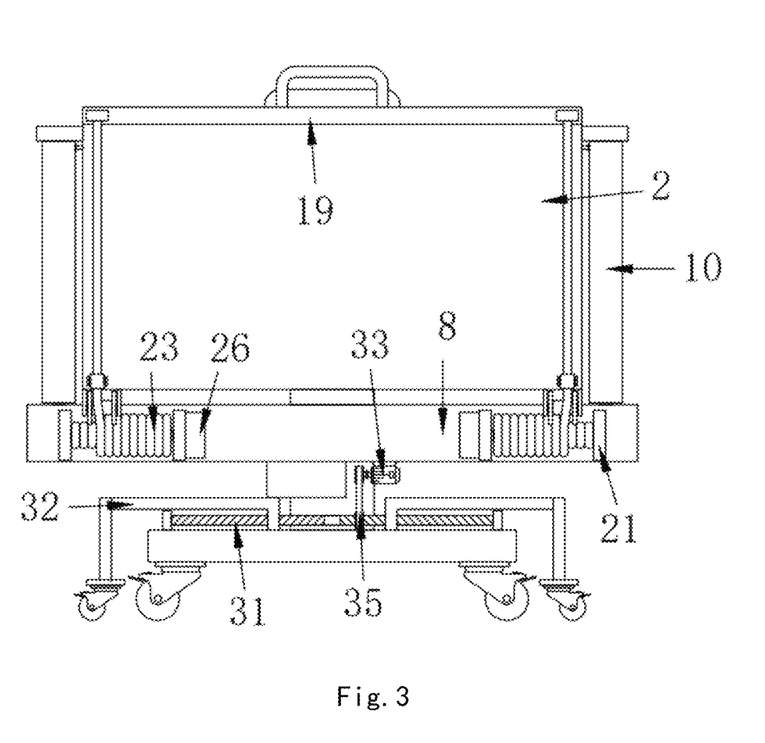
FIG. 3 is a schematic structural front view of a multifunctional electric wave generator for simulation of brain wave and control method thereof in the present disclosure.
Figure 4:
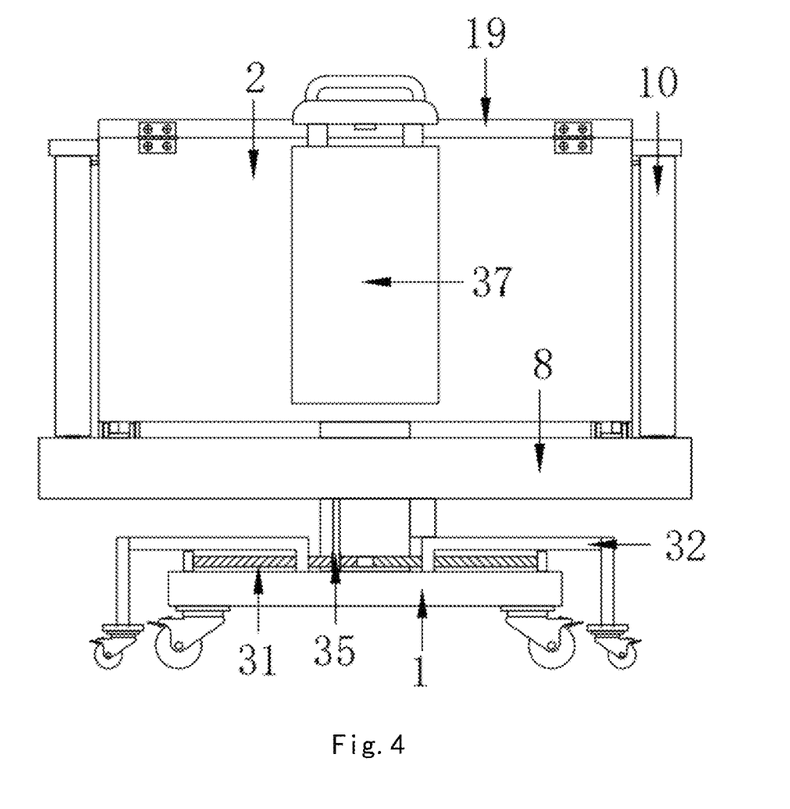
FIG. 4 is a schematic structural rear view of a multifunctional electric wave generator for simulation of brain wave and control method thereof in the present disclosure.
Figure 5:
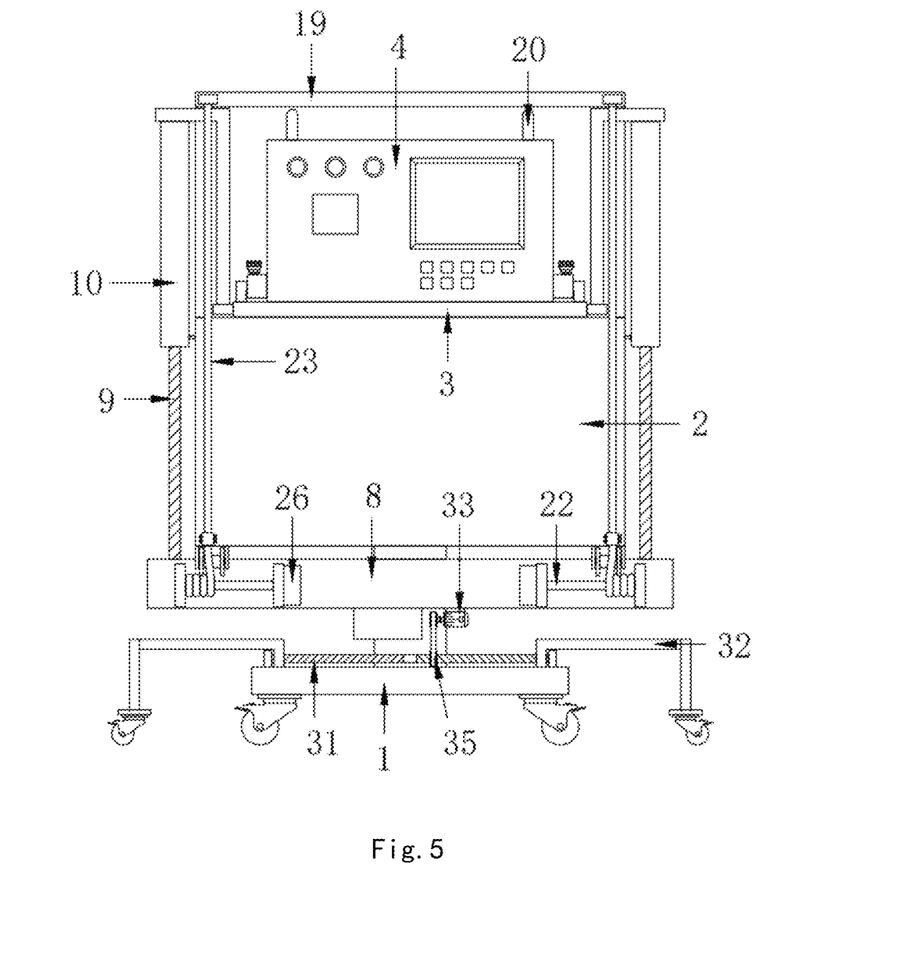
FIG. 5 is a schematic diagram showing the electric wave generator ascending up in the present disclosure.
Figure 6:
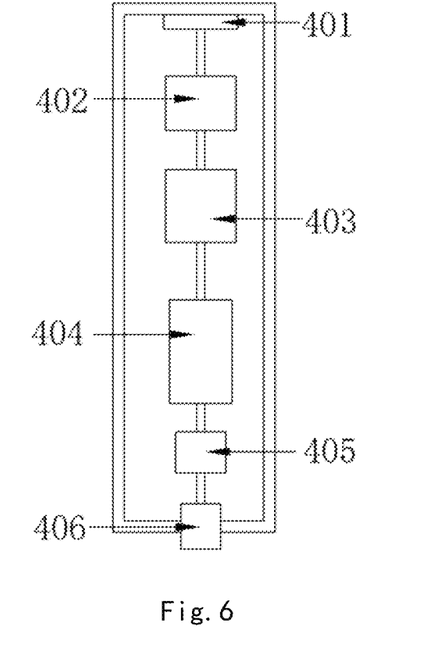
FIG. 6 is a schematic diagram showing the internal configuration of the electric wave generator in the present disclosure.

The electric wave generator body 4 includes a housing, a signal receiver 401, a frequency controller 402, a power amplifier 403, a waveform converter 404, an output device 405, and a digital signal processor 406. The signal receiver 401, frequency controller 402, power amplifier 403, waveform converter 404, output device 405, and the digital signal processor 406 are all assembled inside the housing and are interconnected electrically.

When it is necessary to use the wave generator body 4, it is first placed in a specified position. Then, the electric wave generator 4 is slid out of the protective box 2, and the display device is operated to adjust the waveform converter 404 of the electric wave generator body 4, so that the wave generator body 4 simulates brainwave signals generated naturally. The waveform converter 404 adjusts the frequency of the desired brainwave signals, allowing the waveform generator body 4 to release the waveform intensity and duration required by the user, thereby strengthening the brainwaves emitted by the brain. When the human body receives these simulated brainwave signals, the brain generates synchronous brainwaves following these signals, elevating brainwave frequency. By adjusting the waveform of the simulated brainwave signals, it can be used to invigorate or induce sleep for the user. Through combining the electric wave generator with an artificial intelligence (AI) monitoring system, and then setting the intensity of the wave type and the duration required by the users, it is possible to effectively release different levels of brainwave signals to the user.

In an exemplary embodiment, a limit plate 5 is fixedly mounted on one side of the electric wave generator body 4, an L-shaped plate 6 is fixedly mounted on the top of the support plate 3, and the L-shaped plate 6 is slidingly connected to the limit plate 5. A screwing rod 7 is threadedly mounted on the top of the limit plate 5, and the screwing rod 7 is threadedly connected to the L-shaped plate 6.

When maintenance is required on the electric wave generator body 4, the screwing rod 7 is rotated first to move away from the L-shaped plate 6, after which the electric wave generator body 4 can be driven to slid along the support plate 3, causing the electric wave generator body 4 to drive the limit plate 5 away from the L-shaped plate 6, facilitating the disassembly of the electric wave generator body 4 quickly and efficiently. The electric wave generator body is stabilized in the support plate through the sliding connection between the limit plate and the L-shaped plate, which effectively prevents the displacement during operation due to vibration or external forces.

In an exemplary embodiment, the storage mechanism includes a connecting box 8 fixedly mounted on the upright posts of the base 1, a threaded rod 9 rotatably mounted at the top of the connecting box 8, a threaded sleeve 10 set on the threaded rod 9, a connecting plate 11 fixedly mounted on one side of the support plate 3, and a drive mechanism provided on the connecting box 8 for driving the threaded rod 9. One side of the connecting plate 11 extends outside of the protective box 8, and the connecting plate 11 is securely connected to the threaded sleeve 10.

When the electric wave generator body 4 needs to be stored after use, the drive mechanism is first activated to rotate the threaded rod 9. As the threaded rod 9 turns, the threaded sleeve 10 slides along it, causing the threaded sleeve 10 to move down. This downward movement of the threaded sleeve 10 drives the connecting plate 11 to slide, which in turn moves the support plate 3 down. The support plate 3 then slides the electric wave generator body 4 into the protective box 2 for storage. This storage process is relatively quick. The wave generator body can be stored by the storage mechanism for protection, ensuring its safety when not in use and providing effective protection.

One side of the threaded sleeve 10 is provided with a guide groove 28, in which a guide rod 29 is fixedly installed. A guide block 30 is slidably mounted on the guide rod 29, and the guide block 30 is fixedly connected to one side of the protective box 2. When the threaded rod 9 drives the threaded sleeve 10 to slide, the guide rod 29 inside the guide groove 28 of the threaded sleeve 10 slides along the guide block 30, thereby causing the guide block 30 to limit the sliding movement of the guide rod 29, ensuring the smooth sliding of the threaded sleeve 10.

Figure 7:
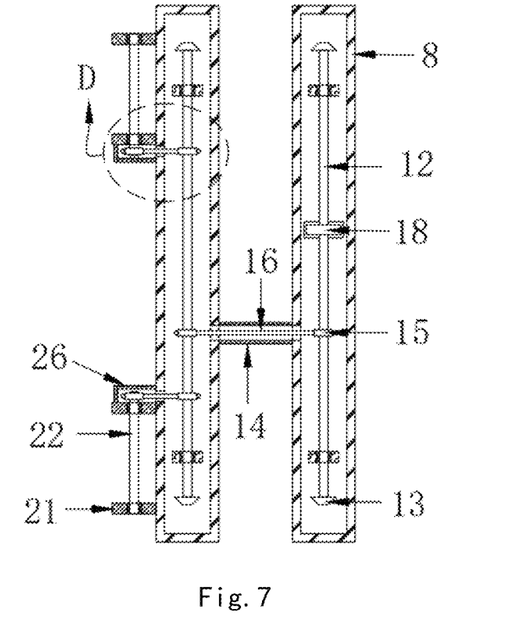
FIG. 7 is a schematic diagram of a connecting box in the present disclosure.
Figure 8:
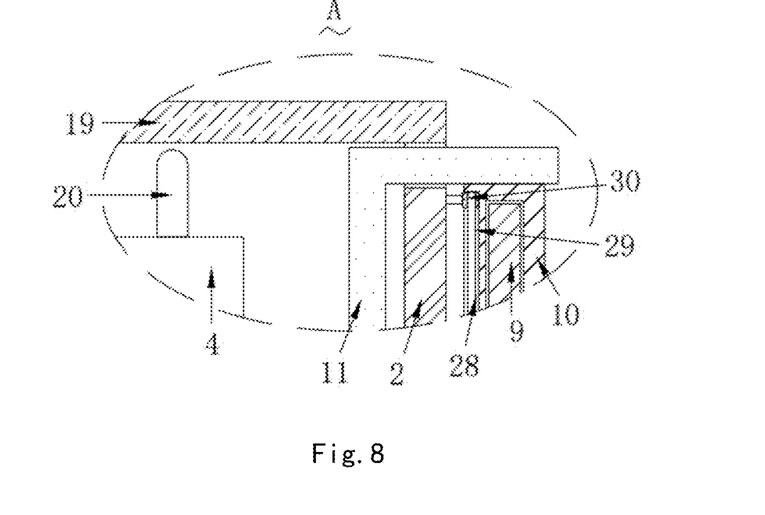
FIG. 8 is an enlarged structural schematic view of a part A in FIG. 1.
Figure 9:
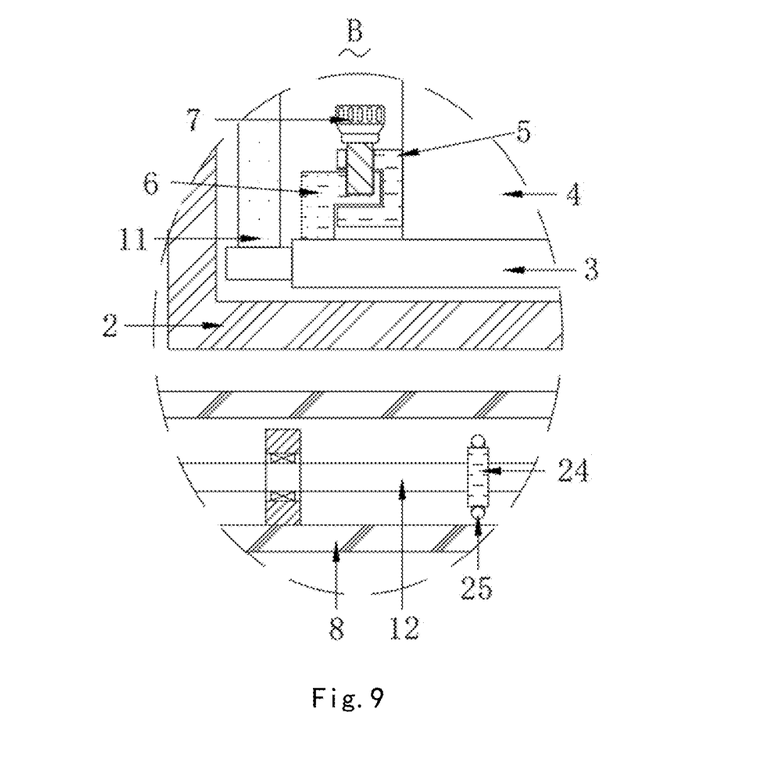
FIG. 9 is an enlarged structural schematic view of a part B in FIG. 1.
Figure 10:
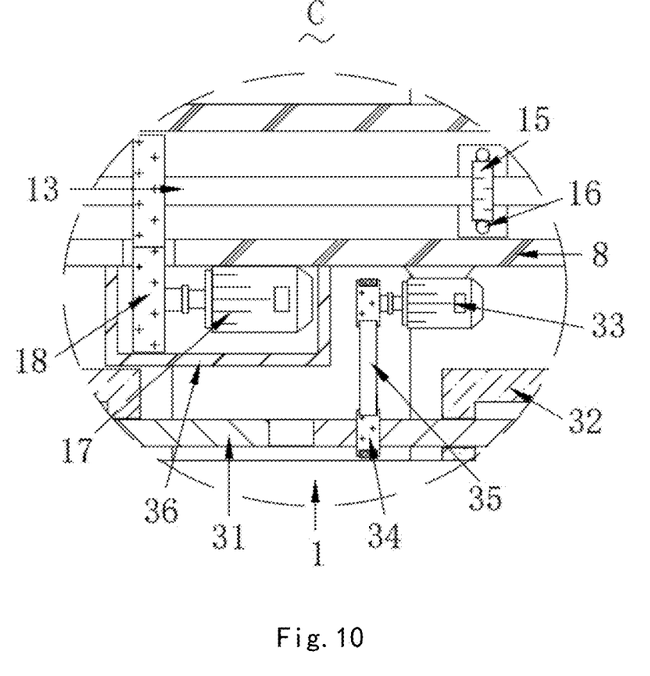
FIG. 10 is an enlarged structural schematic view of a part C in FIG. 1.
Figure 11:
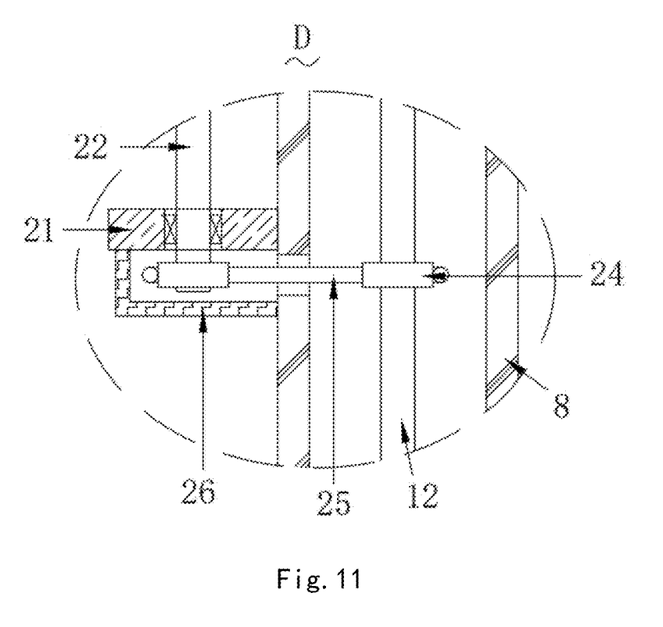
FIG. 11 is an enlarged structural schematic view of a part D in FIG. 1.
Figure 12:
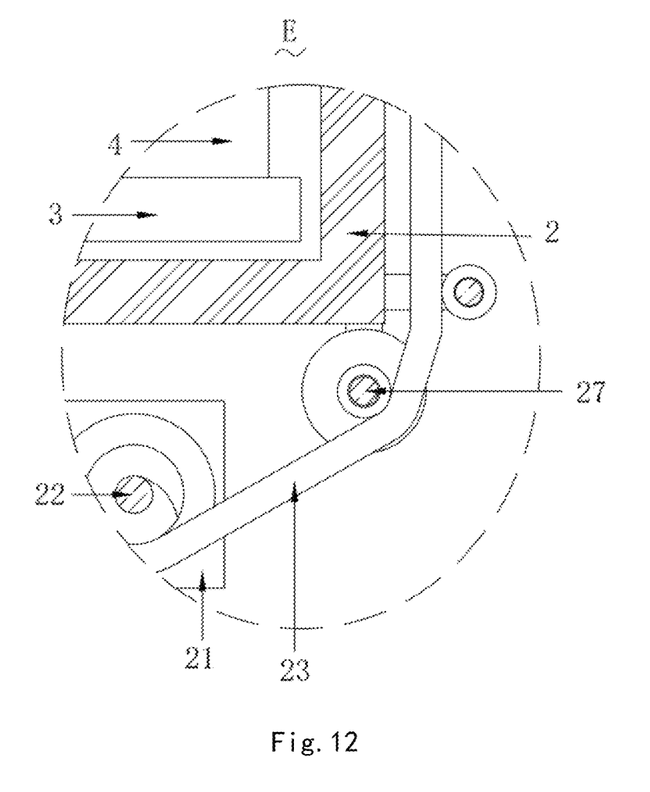
FIG. 12 is an enlarged structural schematic view of a part E in FIG. 1

In an exemplary embodiment, the drive mechanism includes a connecting piece fixedly mounted in the connecting box 8, a rotating lever 12 rotationally mounted on the connecting piece, a junction box 14 fixedly mounted on one side of the connecting box 8, a first sprocket 15 fixedly socketed to the rotating lever 12, connected to a first chain 15 that passes through the junction box 14 and meshes with the first sprocket 15, a first motor 17 fixedly mounted at the bottom of the connecting box 8, and a set of drive gears 18 fixedly socketed to the output shaft of the first motor 17 and the rotating lever 12 respectively, with the drive gears 18 meshing with each other. The the rotating lever 12 and the threaded rod 9 are both fixedly sheathed with conical gears 13, with a set of the conical gears 13 meshing with each other.

When it is necessary to store or raise the electric wave generator body 4, the first step is to start the first motor 17, which drives the output shaft of the first motor 17 to rotate the drive gears 18. This rotation of the drive gears 18 drives the rotating lever 12, which in turn drives the conical gears 13 to rotate the threaded rod 9, causing the threaded rod 9 to perform sliding operation on the threaded sleeve 10. Simultaneously, as the rotating shaft 12 turns, it synchronously drives the first sprocket 15 to rotate, thereby driving the first chain 16 and causing it to synchronize the rotation of a set of first sprockets 15, leading to the synchronous up and down movement of a set of threaded sleeves 10. Through the dual transmission of conical gears 13 and the first chain 16, the drive mechanism efficiently transfers the power from the first motor 17 to the threaded rod 9, ensuring the quick accommodating and unfolding of the electric wave generator body 4.

In an exemplary embodiment, the top of protective box 2 is in an opening shape, a cover plate 19 is hingedly connected to the top of the protective box 2, the top of the cover plate 19 is fixedly mounted with a handle, and the top of the electric wave generator body 4 is assembled with a push rod 20.

When the electric wave generator body 4 moves upwards, it drives the push rod 20 to slide synchronously, causing the push rod 20 to push out the cover plate 19. This action allows the cover plate 19 to rotate along the protective box 2, facilitating the movement of the electric wave generator body 4 outside the protective box 2. The setting of the protective box 2 effectively protects the electric wave generator body 4 from external environmental influences. The setting of the protective box 2 effectively protects the main body 4 of the radio wave generator from external environmental influences. By pushing out the cover plate 19 with the top rod 20, the cover plate 19 is rotated away from the protective box 2, allowing for automatic closing of the cover plate 19, making the operation more convenient.

In an exemplary embodiment, a notch is provided on one side of the protective box 2, the notch is adapted to the connecting plate 11.

By combining the notch with the connecting plate 11, the connecting plate 11 can be retracted effectively, reducing the entry of external dust into the protective box 2.

In an exemplary embodiment, one side of the connecting box is fixedly equipped with a mounting tab 21, on which a connecting bar 22 is pivotally mounted, the connecting bar 22 is wrapped with a rope 23, the top end of the rope 23 is fixedly connected to one side of the cover plate 19.

The rope 23 is used in conjunction with the connecting bar 22, making it easier and more effortless for users to operate the electric wave generator body 4. There is no need to manually open or close the cover plate 19, which not only improves work efficiency but also enhances the user's operating experience. Additionally, the rope 23 provides a stable and reliable control over the opening and closing of the cover plate 19, thereby avoiding safety hazards caused by improper operation. By winding the rope 23 around the connecting bar 22, the cover plate 19 can be automatically opened and closed without manual intervention, offering a better user experience.

In an exemplary embodiment, the connecting bar 22 and rotating lever 12 are both equipped with a second sprocket 24, and a second chain 25 is wrapped around the two second sprockets 24, engaging with both of them.

The linkage between the rotating lever 12 and the connecting bar 22 is achieved through the transmission of the second sprockets 24 and the second chain 25. This design allows the various components of this device to collaborate more closely, enhancing the overall operational coordination and consistency. The rotation of the second sprocket 24 is driven by the second chain 25, which in turn synchronously drives the rotating lever 12 to rotate the connecting bar 22, enabling synchronous release or retraction of the rope 23 and the threaded sleeve 10. This effectively reduces operating costs and provides a better user experience.

In an exemplary embodiment, a protective cover 26 is fixedly mounted on the mounting tab 21, and the protective cover 26 is placed on the second sprocket 24 located on the connecting bar 22.

The protective cover 26 is used to protect the second sprocket 24 and the second chain 25, ensuring that external dust does not come into contact with them, thus helping to mitigate wear and tear.

In an exemplary embodiment, one side of the protective box 2 is equipped with a set of pulleys 27, which come into rotating contact with the rope 23.

The pulleys 27 are used to guide the rope 23, ensuring smooth sliding and facilitating the opening and closing of the cover plate 19.

Figure 13:
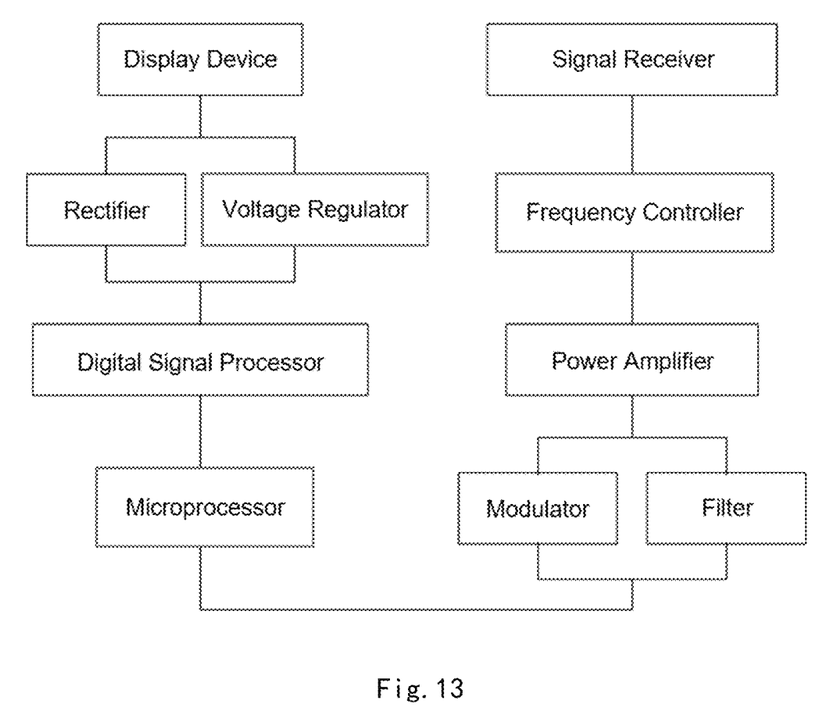
FIG. 13 is a flow diagram of the electric wave generator in the present disclosure.

The present disclosure further provides a control method for a multifunctional electric wave generator for simulation of brain wave, including following steps:

Step one: Ensuring the power supply is stable, connecting the power and ground lines correctly, activating the electric wave generator 4 and allowing it to warm up to improve the frequency stability.

Step two: Selecting or setting a modulation mode as needed, which includes amplitude modulation, frequency modulation, and phase modulation, choosing appropriate filters to filter out clutter or noise from the output signal, then setting or adjusting various parameters, such as waveform type, frequency, amplitude, through a microprocessor to ensure stable DC power supply to the internal circuit of the electric wave generator body 4.

Step three: Selecting the desired waveform type through a waveform converter 404, which includes sine wave, square wave, and triangle wave, setting the desired range of signal output frequency range by a frequency controller 402, adjusting a fine-tuning knob or a keyboard to input the precise frequency, adjusting the output power of the power amplifier 403 as needed to ensure sufficient signal strength, and monitoring the waveform, frequency, amplitude, and other parameters of the output signal in real-time through a display device, utilizing a digital signal processor 406 to further process and optimize the output signal.

Step four: Stimulating the user's brain to be active.

When used in schools, as students often feel drowsy or distracted during class, the device is then moved to the classroom, and the electric wave generator body 4 is slid out of the protective box 2. Subsequently, following steps one to three, the electric wave generator body 4 is operated to coordinate its various components. This allows the electric wave generator body 4 to continuously emit high-frequency alpha waves or mid-low frequency beta waves. In a closed environment such as a classroom, the wave generator's waves have a significant influence, creating a sense of excitement in the brains of students and teachers, helping them stay alert, absorb knowledge better, stimulate creativity, and enhance learning abilities.

Step Five: Inducing users to sleep.

When assistance is required to improve the quality of sleep for insomniacs, follow steps one to three to operate the electric wave generator body 4 to emit brainwave-like signals suitable for inducing sleep, covering the entire space to alter the indoor magnetic field and reduce the influence of other waves in the room, providing relaxing signals to the user's brain to facilitate quicker onset of sleep. By emitting alpha and other waves that relax the brain and promote sleep, the electric wave generator body 4 can effectively reduce the frequency of medication for individuals with insomnia and depression, improving the mood of individuals with depression.

In order to further improve the effectiveness of this device, in addition to the aforementioned aspects, the present disclosure also includes the following embodiments.

In another embodiment of the present disclosure, a bidirectional screw 31 is rotatably mounted at the top of the base 1. A support wheel 32 is threaded onto the bidirectional screw 31. A second motor 33 is fixedly installed at the bottom of the connecting box 8. The output shaft of the second motor 33 and the bidirectional screw 31 are both fitted with limit wheels 34, with a belt 35 mounted on a set of limit wheels 34.

When using this device and sliding the electric wave generator body 4 out of the protective box 2, the second motor 33 is first activated. The output shaft of the second motor 33 drives the limit wheel 34 to rotate, which in turn drives the belt 35 to rotate. The rotation of the belt 35 drives the bidirectional screw 31, causing the support wheel 32 to slide away from the base 1, providing additional support to the base 1 to ensure that the electric wave generator body 4 does not tip over. The design of the bidirectional screw 31 and the support wheel 32 allows the electric wave generator body 4 to move flexibly in the horizontal direction, making it convenient for the equipment to be adjusted or moved when needed, while ensuring the protective box 2 remains stable. This not only improves the safety of using the electric wave generator body 4 but also ensures smoother movement during repositioning.

In an exemplary embodiment, a connecting cover 36 is fixedly mounted at the bottom of the connecting box 8, covering the first motor 17, while a retractable handle 37 is mounted on one side of the protective box 2.

The retractable handle 37 allows users to easily grip and move the entire device, making operations more convenient and effortless.

In an exemplary embodiment, the electric wave generator body 4 is equipped with a modulator, a filter, a microprocessor, a rectifier, a voltage regulator, and a display device, all of which are respectively connected to the signal receiver 401, frequency controller 402, power amplifier 403, waveform converter 404, output device 405, and digital signal processor 406, establishing communication links.

By using multiple components in conjunction within the electric wave generator body 4, negative oxygen ions can be produced, which can help elevate mood, strengthen the immune system, and improve sleep quality. This enhances the effectiveness of the product. Additionally, when using this device, it is equipped with an artificial intelligence (AI) monitoring system, allowing for the unified setting of the desired wave type intensity and duration by the user during the process, enabling automatic switching by the AI system.

In conclusion, compared to related technologies, this device can simulate various waveforms, making it suitable for use by different groups and having high applicability.

It should be understood that in the various embodiments provided in this application, the disclosed device can be implemented in other ways.

The above embodiments are only intended to illustrate the technical solutions of the present disclosure, rather than limit the scope of the disclosure. Obviously, the described embodiments are only some embodiments of the present disclosure, not all embodiments. Based on these embodiments, all other embodiments obtained by those skilled in the art without exercising inventive labor belong to the scope of protection of the present disclosure. Although the above embodiments provide a detailed description of the present disclosure, those skilled in the art can still, without conflicting, combine, add, or make other adjustments to the features of the embodiments of the present disclosure according to the circumstances, without exercising inventive labor, in order to obtain different technical solutions that are not depart from the essence of the present disclosure. These technical solutions also fall within the scope of protection of the present disclosure.

What is claimed is:

1. A multifunctional electric wave generator for simulation of brain wave, comprising:
    a base;
    a protective box fixedly mounted on a top of the base;
    a support plate located inside the protective box;
    an electric wave generator body placed on the support plate, comprising a housing, a signal receiver, a frequency controller, a power amplifier, a waveform converter, an output device, and a digital signal processor; the signal receiver, frequency controller, power amplifier, waveform converter, output device, and the digital signal processor are all assembled inside the housing and are interconnected electrically; and
    a storage mechanism disposed on the protective box for storing the electric wave generator body;
    wherein a limit plate is fixedly mounted on at least one side of the electric wave generator body, an L-shaped plate is fixedly mounted on a top of the support plate, the L-shaped plate is slidingly connected to the limit plate, and a screwing rod is threadedly mounted on a top of the limit plate, and the screwing rod is threadedly connected to the L-shaped plate;
    wherein the storage mechanism comprises:
    a connecting box fixedly mounted on upright posts of the base;
    a threaded rod rotatably mounted at a top of the connecting box;
    a threaded sleeve set on the threaded rod;
    a connecting plate fixedly mounted on at least one side of the support plate, one side of the connecting plate extending outside of the protective box, the connecting plate being securely connected to the threaded sleeve; and
    a drive mechanism provided on the connecting box for driving the threaded rod.

2. The multifunctional electric wave generator for simulation of brain wave according to claim 1, wherein the drive mechanism comprises:
    a connecting piece fixedly mounted in the connecting box;
    a rotating lever rotationally mounted on the connecting piece, with conical gears fixedly sheathed on both the rotating lever and the threaded rod, where a set of the conical gears mesh with each other;
    a junction box fixedly mounted on one side of the connecting box;
    a first sprocket fixedly socketed to the rotating lever, connected to a first chain that passes through the junction box and meshes with the first sprocket;
    a first motor fixedly mounted at a bottom of the connecting box; and
    a set of drive gears fixedly socketed to an output shaft of the first motor and the rotating lever respectively, with the set of drive gears meshing with each other.

3. The multifunctional electric wave generator for simulation of brain wave according to claim 2, wherein a top of the protective box is in an opening shape, a cover plate is hingedly connected to the top of the protective box, a top of the cover plate is fixedly mounted with a handle, and a top of the electric wave generator body is assembled with a push rod.

4. The multifunctional electric wave generator for simulation of brain wave according to claim 3, wherein at least one side of the connecting box is fixedly equipped with a mounting tab, on which a connecting bar is pivotally mounted, the connecting bar is wrapped with a rope, a top end of the rope is fixedly connected to at least one side of the cover plate.

5. The multifunctional electric wave generator for simulation of brain wave according to claim 4, wherein the connecting bar and the rotating lever are both equipped with a second sprocket, and a second chain is wrapped around the two second sprockets, engaging with both of them.

6. The multifunctional electric wave generator for simulation of brain wave according to claim 5, wherein a protective cover is fixedly mounted on the mounting tab, and the protective cover is placed on the second sprocket located on the connecting bar.

7. The multifunctional electric wave generator for simulation of brain wave according to claim 1, wherein a notch is provided on at least one side of the protective box, the notch is adapted to the connecting plate.

8. A control method of the multifunctional electric wave generator for simulation of brain wave according to claim 1, comprising the following steps:
    step one: ensuring a power supply is stable, connecting power and ground lines correctly, activating the electric wave generator and allowing it to warm up to improve-frequency stability;
    step two: selecting or setting a modulation mode as needed, wherein the modulation modes are selected from the group of amplitude modulation, frequency modulation, and phase modulation, choosing appropriate filters to filter out clutter or noise from an output signal, then adjusting parameters, wherein the parameters are selected from the group of waveform type, frequency, amplitude, through a microprocessor to ensure stable DC power supply to an internal circuit of the electric wave generator body;

step three: selecting a desired waveform type through a waveform converter, wherein the waveform type is selected from the group of sine wave, square wave, and triangle wave, setting a desired range of signal output frequency range by a frequency controller, adjusting a fine-tuning knob or a keyboard to input a precise frequency, adjusting an output power of the power amplifier as needed to ensure sufficient signal strength, and monitoring waveform, frequency, amplitude, and other parameters of the output signal in real-time through a display device, utilizing a digital signal processor to further process and optimize the output signal.

* * * * *